US00PP17346P2

(12) United States Plant Patent
Radler

(10) Patent No.: US PP17,346 P2
(45) Date of Patent: Jan. 9, 2007

(54) SHRUB ROSE PLANT NAMED 'RADCOR'

(50) Latin Name: *Rosa hybrida*
Varietal Denomination: Radcor

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 2 days.

(21) Appl. No.: 11/152,247

(22) Filed: Jun. 15, 2005

(51) Int. Cl.
*A01H 5/00* (2006.01)

(52) U.S. Cl. ..... Plt./102

(58) Field of Classification Search ..... Plt./102, Plt./107, 141, 148, 149
See application file for complete search history.

*Primary Examiner*—Howard J. Locker
(74) *Attorney, Agent, or Firm*—Buchanan Ingersoll & Rooney PC

(57) ABSTRACT

A new and distinct variety of landscape shrub rose plant is provided which forms in abundance on a substantially continuous basis attractive single blossoms that are light coral pink with a yellow eye. The vegetation is vigorous and the growth habit is round and bushy. Attractive ornamental satiny green foliage is formed. Excellent disease resistance to blackspot and rust is exhibited. The new variety is particularly well suited for growing as distinctive ornamentation in the landscape.

1 Drawing Sheet

Botanical/commercial classification: *Rosa hybrida*/Shrub Rose Plant.
Varietal denomination: cv. Radcor.

SUMMARY OF THE INVENTION

The new variety of *Rosa hybrida* landscape shrub rose plant of the present invention was created at Greenfield, Wis., U.S.A. by artificial pollination wherein two parents were crossed which previously had been studied in the hope that they would contribute the desired characteristics. The female parent (i.e., the seed parent) was the 'RADtee' variety (non-patented in the United States). The male parent (i.e., the pollen parent) of the new variety was the 'RADral' variety (non-patented in the United States). The parentage of the new variety can be summarized as follows:

'RADtee'×'RADral'.

The seeds resulting from the above pollination were sown and small plants were obtained which were physically and biologically different from each other. Selective study resulted in the identification of a single plant of the new variety.

It was found that the new variety of landscape shrub rose plant of the present invention possesses the following combination of characteristics:

(a) abundantly and substantially continuously forms attractive single blossoms that are light coral pink with a yellow eye, (b) exhibits a round and bushy growth habit, (c) forms vigorous vegetation, (d) forms attractive ornamental green foliage with a satiny finish, and (e) exhibits excellent resistance to blackspot and rust.

The blooming cycle is believed to be one of the longest observed to date for a rose plant.

The new variety well meets the needs of the horticultural industry. It can be grown to advantage as attractive ornamentation in parks, gardens, public areas, and in residential settings. It is particularly well suited for growing in the landscape. The light coral pink blossoms contrast nicely with the satiny green foliage.

The new variety of the present invention also can be readily distinguished from its ancestors. More specifically, the 'RADtee' variety forms blossoms having approximately 12 petals which are white with a pink edge, and the 'RADral' variety forms blossoms having approximately 16 petals which are deep orange-pink in coloration.

The characteristics of the new variety have been found at Waso, Calif., U.S.A., and at West Grove, Pa., U.S.A., to be homogeneous and stable and are strictly transmissible by asexual propagation such as budding, grafting, and the rooting of cuttings from one generation to another. The new variety reproduces true to type by such asexual propagation.

The new variety has been named the 'Radcor' variety.

BRIEF DESCRIPTION OF THE PHOTOGRAPHS

The accompanying photograph shows, as nearly true as it is reasonably possible to make the same in a color illustration of this character, typical blossoms and foliage of the new variety. The illustrated rose plant of the new variety was approximately three years of age and was observed during June while growing outdoors on its own roots at West Grove, Pa., U.S.A.

DETAILED DESCRIPTION

The chart used in the identification of colors is that of The Royal Horticultural Society (R.H.S. Colour Chart), London, England. The description is based on the observation of three year-old specimens of the new variety during June while growing outdoors on their own roots near West Grove, Pa., U.S.A.

Class: Landscape Shrub Rose.

Plant:

*Height.*—Approximately one meter on average at the end of the growing season.

*Width.*—Approximately one meter on average at the end of the growing season.

*Habit.*—Round, and bushy.

Branches:

*Color.*—Young stems: near Yellow-Green Group 144B with some highlights of Red Group 53A. Adult wood: Yellow-Green Group 144B suffused with Greyed-Purple Group 184A.

*Thorns.*—Size: approximately 1 to 1.5 cm in length on average with some smaller bristles/prickles near the peduncle. Color: Brown Group 200A.

Leaves:

*Stipules.*—Approximately 24 mm in length, approximately 10 mm in width, parallel with the auricle facing outward, and Yellow-Green Group 144B in coloration.

*Petioles.*—Upper surface: Yellow-Green Group 144B with highlights of Greyed-Purple Group 184A and some prickles. Under surface: Yellow-Green Group 144B.

*Leaflets.*—Number: 3, 5, and 7. Shape: ovate with a serrulate margin, rounded base, and an acuminate tip. Margins: serrulate. Texture: Smooth. Leaflet size: commonly approximately 5.5 cm in length and approximately 3.7 cm in width on average for a terminal leaflet. Overall appearance: very dense, leathery, and medium green in coloration, with a satiny finish. Color (young foliage): Upper surface: Green Group 141D with highlights of Greyed-Purple Group 187A. Under surface: Greyed-Purple Group 187B. Color (adult foliage): Upper surface: commonly between Yellow-Green Group 147A and Green Group 136A. Under surface: Yellow-Green Group 147B with some Yellow-Green Group 148D.

Inflorescence:

*Number of flowers.*—Commonly approximately 3 to 10 blooms on average in a cluster.

*Peduncle.*—Medium green, Group Group 143A, with some prickles, approximately 3 cm in length on average, and approximately 2.1 mm in diameter.

*Sepals.*—Upper surface: between Yellow-Green Group 144A and Yellow-Green Group 144B. Under surface: Yellow-Green Group 144A with areas of White Group 155D and some pubescence. Number: five.

*Buds.*—Shape: slender. Length: approximately 2.5 cm on average. Size: small to medium. Color (when opening): Upper surface: Yellow Group 3A at the base, Yellow-Orange Group 21A towards the middle, and Red Group 39B at the apex. Under surface: Yellow Group 3C at the base, Yellow-Orange Group 21C towards the middle, and Red Group 39B at the apex.

*Flower.*—Form: single and informal. Diameter: approximately 4.5 cm. on average. Color (when opening begins): Upper surface: Yellow Group 3A at the base, Yellow-Orange Group 21A towards the middle, and Red Group 39B at the apex. Under surface: Yellow Group 3C at the base, Yellow-Orange Group 21C at the middle, and Red Group 39B at the apex. Color (when blooming): Upper surface: Yellow Group 3A at the base, and Red Group 55A at the apex. Under surface: Yellow Group 3D at the base, and Red Group 55A at the apex. Color (at end of blooming): Upper surface: Yellow Group 3D at the base, and Red Group 55D at the apex. Under surface: Yellow Group 3D at the base fading to Red Group 55D at the apex. Fragrance: mild spice. Petal form: wedge-shaped with a curled apex. Petal number: approximately 5 on average. Petaloids: none observed. Lasting quality: blossoms commonly last approximately two weeks on the plant and approximately three weeks when cut and placed in a vase. Petal drop: very good, the petals drop cleanly and freely. Stamen number: approximately 80 on average. Anthers: Greyed-Yellow Group 162B in coloration. Filaments: approximately 8 mm in length on average, and Yellow Group 11A in coloration. Pistils: are separate and free, and number approximately 20 on average. Stigmas: Yellow Group 13C in coloration. Styles: Red Group 44B in coloration. Receptacle: With achenes standing on the bottom and wall. Hips: Commonly approximately 12 mm in length, approximately 18 mm in width, and Greyed-Orange Group 168B in coloration.

Development:

*Vegetation.*—Vigorous and strong.

*Blossoming.*—Abundant and substantially continuous.

*Resistance to diseases.*—Excellent with respect to blackspot and rust.

*Formation of hips/seeds.*—Plants begin to form hips late in the season at West Grove, Pa., U.S.A., usually at approximately October 1$^{st}$.

I claim:

1. A new and distinct landscape shrub rose plant characterized by the following combination of characteristics:

(a) abundantly and substantially continuously forms attractive single blossoms that are light coral pink with a yellow eye, (b) exhibits a round and bushy growth habit, (c) forms vigorous vegetation, (d) forms attractive ornamental green foliage with a satiny finish, and (e) exhibits excellent resistance to blackspot and rust;

substantially as herein shown and described.

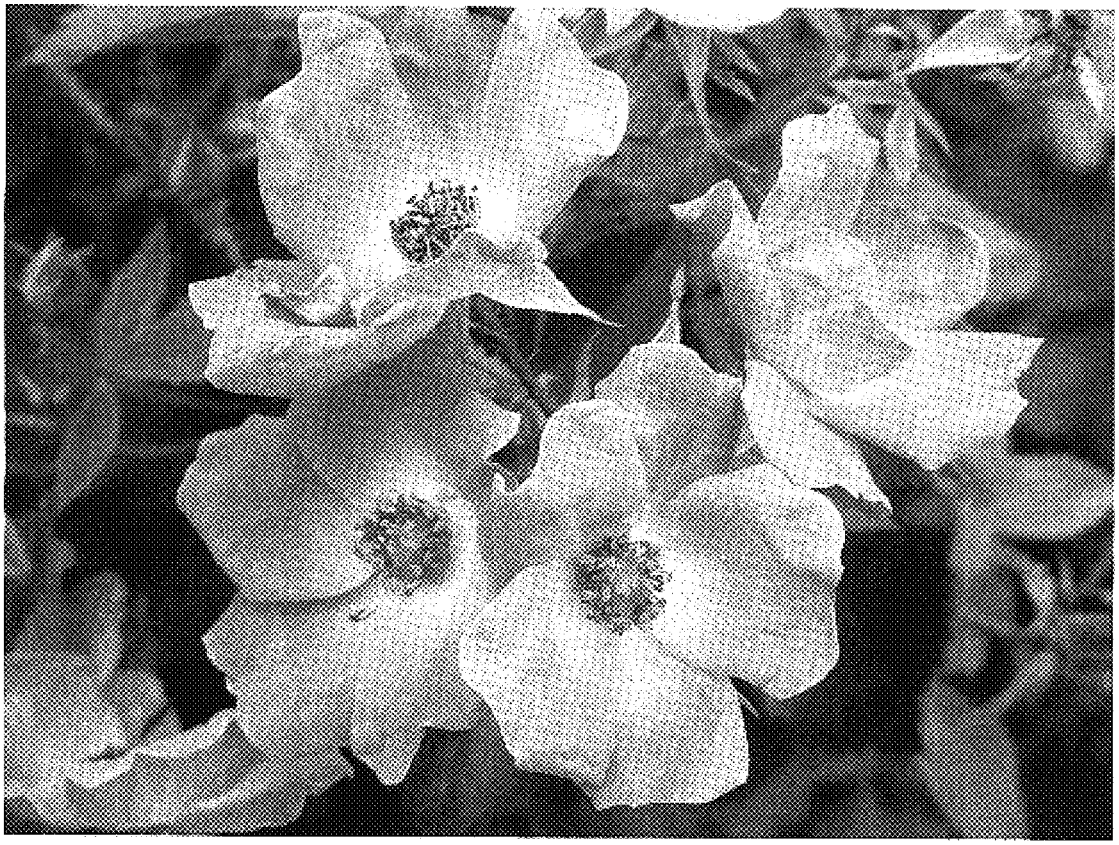

* * * * *